United States Patent [19]

Kusumoto et al.

[11] Patent Number: 5,386,033
[45] Date of Patent: Jan. 31, 1995

[54] 2-AMINOPYRIDINE COMPOUNDS

[75] Inventors: Shoichi Kusumoto, Osaka; Sumihiro Hase, Hyogo; Koichi Fukase, Osaka, all of Japan

[73] Assignee: Seikagaku Kogyo Kabushiki Kaisha (Seikagaku Corporation), Tokyo, Japan

[21] Appl. No.: 31,476

[22] Filed: Mar. 15, 1993

[30] Foreign Application Priority Data

Mar. 13, 1992 [JP] Japan .................................. 4-088314

[51] Int. Cl.$^6$ .......................................... C07D 213/02
[52] U.S. Cl. ...................................... 546/309; 546/311
[58] Field of Search ................................ 546/311, 309

[56] References Cited

U.S. PATENT DOCUMENTS 2,807,619  9/1957  Cislak ................................. 546/311
4,975,533 12/1990  Kondo et al. ....................... 536/55.3

OTHER PUBLICATIONS

Goto et al., *J. of Antibiotics*, vol. 37, (805, pp. 532–545, 1984.
Balkovec et al., *J. of Antibiotics*, vol. 44, No. 10, pp. 1122–1127, 1991.
Hase et al. J. Biochem., 90, 407–414 (1981).
J. Biochem., 95, 197–203 (1984), Hase et al.
Agric Biol. Chem., 54(8), 2169–2170 (1990), Kondo et al.
Farmaco (Pavia) Ed. Sci. 14, 594–597 (1959).
JP-A-1-141356 Abstract (1989).

*Primary Examiner*—C. Warren Ivy
*Assistant Examiner*—Zinna N. Davis
*Attorney, Agent, or Firm*—Sughrue, Mion, Zinn, Macpeak & Seas

[57] ABSTRACT

2-Aminopyridine derivatives having a bifunctional or unifunctional structure and capable of serving as reactants in synthetically converting organic compounds, such as carbohydrates, proteins, lipids or polymer resins, to desired conjugated structures suited for various purposes and detectable by fluorescence spectrometry with high sensitivity, a fluorescent labeling agent comprising the same, and methods of their production are disclosed.

1 Claim, No Drawings

2-AMINOPYRIDINE COMPOUNDS

FIELD OF THE INVENTION

The present invention relates to novel 2-aminopyridine derivatives and a method of producing the same and, more particularly, to bifunctional crosslinking agents usable in fluorescence labeling of biological substances, such as carbohydrates, proteins, amino acids, lipids and nucleic acids, for assaying the same in various ways and capable of crosslinking said biological substances or such a biological substance with a synthetic resin.

BACKGROUND OF THE INVENTION

In recent years, various techniques which are highly sensitive and enable assaying trace amounts of samples have been proposed for investigating the structure-activity relationships of complex or conjugated carbohydrates (glycoconjugate) such as glycoproteins.

For example, a method of microanalysis of sugar chains comprises tritiating on the occasion of conversion of the reducing terminus to a sugar alcohol group and utilizing the radioactivity of tritium. The detection sensitivity is good, namely at the picomole level. However, since tritium is a radioactive substance, various restrictions are inevitable.

A high-sensitivity assay method free of such restrictions is known, which uses an organic compound such as 2-aminopyridine as a fluorescent labeling agent [e.g. S. Hase et al., Journal of Biochemistry, 95, 197–203 (1984)].

This method comprises reacting the reducing terminus of a carbohydrate or a sugar chain with the 2-amino group of said organic compound, reducing the resulting Schiff base and detecting the product by its fluorescence. It is disclosed that the sensitivity is at the picomole level, like in the above case.

The above fluorescent labeling agent is effective in the structure analysis of carbohydrate chains but, because of its unifunctionality, cannot cause formation of conjugates of carbohydrates with other biological substances such as proteins, amino acids, lipids and nucleic acids. Therefore, it is not fully satisfactory for global analysis.

SUMMARY OF THE INVENTION

Accordingly, an object of the present invention is to provide 2-aminopyridine derivatives which have a bifunctional structure and can cause formation of a desired conjugate structure between biological substances such as carbohydrates, proteins, amino acids, nucleic acids, lipids, etc. or between such a substance and a synthetic resin; 2-aminopyridine derivatives which are derived from said 2-aminopyridine derivatives by binding the amino group of the latter to carbohydrates and have a unifunctional structure capable of forming a conjugate structure upon further binding of such a biological substance as mentioned above or a polymer resin, for instance; and methods of producing them. Another object of the invention is to provide bifunctional or unifunctional fluorescent labeling agents which, upon reaction with biological substances as mentioned above, give conjugates detectable with high sensitivity. A further object is to provide bifunctional crosslinking agents capable of forming conjugates which are similar in structure to conjugates occurring in the living body, such as glycoproteins and glycolipids.

In one aspect thereof, the present invention provides 2-aminopyridine derivatives of the formula (a)

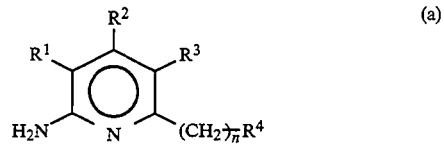

wherein $R^1$, $R^2$ and $R^3$ may be the same or different and each independently is a hydrogen atom or a lower alkyl group containing 1 to 4 carbon atoms, $R^4$ is a carboxyl group or a carboxyalkyl group of the formula $-(CH_2)_m COOH$, a cyano group or a cyanoalkyl group of the formula $-(CH_2)_m CN$, an aminoalkyl group, an alkoxycarbonyl group, an alkyloxycarbonylamino group, a mercapto group, a maleimido group, a hydroxyl group or a halogen atom, and n is an integer of 2 to 20, m being 0 or an integer of 1 to 3.

In another aspect, the invention provides a method of producing compounds (a) of the invention which comprises the steps of:

protecting the amino group of a compound of the formula (b)

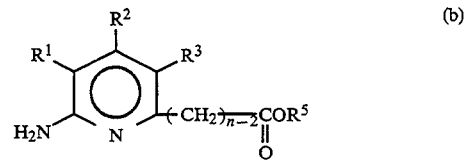

wherein $R^1$, $R^2$ and $R^3$ are as defined above and $R^5$ is a lower alkyl group containing 1 to 4 carbon atoms, with a protective group $R^6$;

reducing the $-CO^2R^5$ group at position 6 to give a compound of the formula (c)

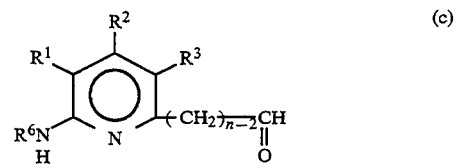

wherein $R^1$, $R^2$ and $R^3$ are as defined above and $R^6$ is an amino-protecting group;

reacting the $-CHO$ group at position 6 of compound (c) with a mating compound capable of condensing with said $-CHO$ group under formation of a carbon-carbon double bond to give a compound of the formula (d)

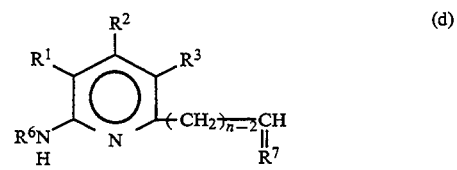

wherein $R^1$, $R^2$ and $R^3$ and $R^6$ are as defined above and $R^7$ is the residue of said mating compound, at least reducing the $-CH=R^7$ group at position 6; and eliminating the protective group $R^6$.

In a further aspect, the invention provides 2-aminopyridine derivatives of the formula (e)

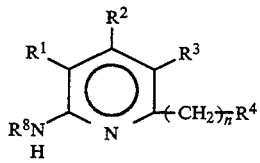
(e)

wherein $R^1$, $R^2$, $R^3$, $R^4$ and n are as defined above and $R^8$ is a carbohydrate compound residue, which are derived from the compounds of formula (a) by coupling thereof, via the amino group at position 2, with a carbohydrate compound at least having a terminal reducing sugar moiety.

In a still further aspect, the invention provides bifunctional fluorescent labeling agents and bifunctional crosslinking agents which comprise the above-mentioned compounds (a) of the invention as well as unifunctional fluorescent labeling agents which comprise the above-mentioned compounds (e).

DETAILED DESCRIPTION OF THE INVENTION

In a preferred embodiment of the invention, those compounds (a) in which $R^4$ is a carboxyl or cyano group are produced by the above method using, as said mating compound, a compound of the formula $R^{4a}CH_2COOR^9$, in which $R^{4a}$ is —$COOR^9$ or —CN and $R^9$ is a lower alkyl group containing 1 to 4 carbon atoms when $R^{4a}$ is —$COOR^9$ and, when $R^{4a}$ is —CN, $R^9$ is a lower alkyl group containing 1 to 4 carbon atoms or a hydrogen atom. The resulting —CH=$R^7$ group, namely —CH=$CR^{4a}COOR^9$, is reduced, followed by decarboxylation of the carboxylic acid moiety or saponification and decarboxylation of the carboxylic acid ester moiety, whereby said —CH=$R^7$ group is converted to —$CH_2CH_2R^4$, in which $R^4$ is —COOH or —CN (synthetic method A).

In another preferred embodiment, those compounds (a) in which $R^4$ is —$(CH_2)_mCN$ or —$(CH_2)_mCOOH$, in which m is 0 or an integer of 1 to 3, are produced by the above method using, as said mating compound, a compound of the formula $Ph_3P=CHR^{4b}$, in which $R^{4b}$ is —$(CH_2)_mCOOR^9$ or —$(CH_2)_mCN$, m is 0 or an integer of 1 to 3, $R^9$ is a lower alkyl group as defined above and Ph is a phenyl group. The resulting —CH=$R^7$ group, namely —CH=$CHR^{4b}$ is reduced, whereby said —CH=$R^7$ group is converted to -$CH_2CH_2R^4$, in which $R^4$ is —$(CH_2)_mCOOH$ or —$(CH_2)_mCN$ (synthetic method B).

In a further preferred embodiment, those compounds (a) in which $R^4$ is an aminoalkyl group of the formula, $(CH_2)_mCH_2NH_2$, in which m is 0 or an integer of 1 to 3, are produced by reducing those compounds (a) in which $R^4$ is a cyano group or a cyanoalkyl group of the formula —$(CH_2)_mCN$, to thereby convert the —CN group to —$CH_2NH_2$ (synthetic method C).

The compounds (a) of the present invention have an amino group, which is a functional group, at position 2 and, at position 6, a functional group represented by $R^4$ and selected from among a carboxyl group or a carboxyalkyl group of the formula —$(CH_2)_mCOOH$, a cyano group or a cyanoalkyl group of the formula —$(CH_2)_mCN$, an aminoalkyl group, an alkoxycarbonyl group, an alkyloxycarbonylamino group, a mercapto group, a maleimido group, a hydroxyl group or a halogen atom, and can be used as bifunctional fluorescent labeling agents capable of labeling other organic compounds by coupling therewith via one or both of the functional groups and also as crosslinking agents capable of crosslinking one organic compound molecule to another via the both functional groups.

The compounds (e) of the invention contain a carbohydrate compound as a substituent on the amino group at position 2 and have, at position 6, a functional group of the same kind as in the compounds (a) of the invention, and can be used as unifunctional fluorescent labeling agents capable of labeling other organic compounds by coupling therewith via said functional group.

[Compounds of the invention]

In the compounds (a) and (e) of the present invention, $R^1$, $R^2$ and $R^3$ which occur on the pyridine ring, may be the same or different and each is selected from among a hydrogen atom and lower alkyl groups containing about 1 to 4 carbon atoms (methyl, ethyl, propyl, isopropyl, etc.). In preferred cases, each of them is a hydrogen atom. The number n in the carbon chain substituent —$(CH_2)_n$— at position 6 of the pyridine ring is not particularly restricted but preferably is 2 to 20, more preferably 2. When n exceeds 20, the hydrophobicity increases and may cause an undesirable hydrophobic interaction. The functional group $R^4$ occurring at the terminus of the above-mentioned carbon chain at position 6 will be described below in more detail.

[Functional groups]

Basically, the functional group ($R^4$) at position 6 of the pyridine ring in the compounds (a) or (e) of the present invention is not limited to any particular species as long as it can form a conjugate with an organic compound to be coupled with said functional group and the conjugate formed can be analyzed by fluorescence spectrometry. As preferred examples, however, there may be mentioned groups selected from among a carboxyl group or a carboxyalkyl group of the formula —$(CH_2)_mCOOH$, a cyano group or a cyanoalkyl group of the formula —$(CH_2)_mCN$, an aminoalkyl group, an alkoxycarbonyl group, an alkyloxycarbonylamino groups and a mercapto group. The alkyl moiety of this group has 1 to 3 carbon atoms. n is an integer of 2 to 20 and m is 0 or an integer of 1 to 3. The functional group may further be a maleimido group, a hydroxyl group or a halogen atom. Usable as a halogen atom are chlorine and bromine.

[Synthesis of compounds (a)]

The compounds (a) of this invention can be produced by any appropriate method. Preferably, however, they are produced by protecting the amino group of compound (b) with a protective group $R^6$, reducing the —$COOR^5$ group at position 6, reacting the resulting compound (c) with a mating compound capable of condensing with the formyl (—CHO) group at said position 6 under formation of a carbon-carbon double bond, at least reducing the —CH=$R^7$ group at position 6 of the resulting compound (d) and eliminating the amino-protecting group $R^6$.

Among the starting compounds (b), those in which n=2 are already known in the art and can be synthesized by a known method [Farmaco (Pavia), Ed. Sci., 14, 594–597 (1959)], for instance. Those in which n is 3 or more are novel compounds. In the compounds (b), $R^5$ contains 1 to 4 carbon atoms, preferably 1 or 2 carbon atoms.

Typical modes of embodiment of the above synthetic method are described in the following.

(Synthetic Method A)

This synthetic method, which is described below in further detail, can be used in synthesizing those compounds (a) in which $R^4$ is a carboxyl group or a cyano group. This method can be outlined by the following reaction scheme.

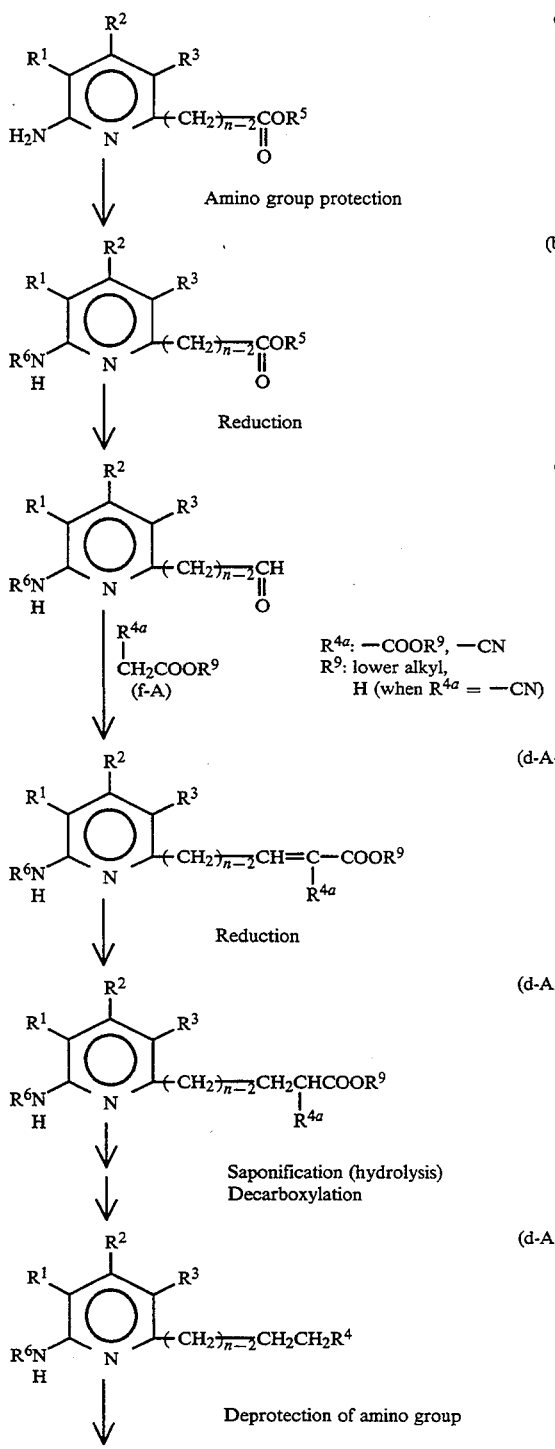

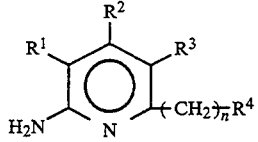

First, a protective group $R^e$ is introduced into the amino group of compound (b). The protective group may be a conventional one, for example an aralkyl group having 7 to 20 carbon atoms such as trityl, diphenylmethyl, benzyl or methoxybenzyl. Generally, the compound (b) is reacted with a halide (e.g. chloride) of such protective group in the presence of a base (e.g. triethylamine) in a solvent such as chloroform at a temperature around room temperature for several hours, preferably about 4.5 hours.

The thus-obtained compound ($b^a$) is reduced for synthesizing the compound (c). For the reduction, a selective reducing agent such as diisobutylhydridoaluminum (DIBAL-H) or lithium tri-tert-butoxyaluminum hydride may be used. The reaction can be carried out in a solvent, such as toluene, under cooling (e.g. at $-70°$ C.) and will be complete in several tens of minutes, preferably about 30 minutes.

Then, the compound (c) is reacted with a compound of the formula $R^{4a}CH_2COOR^9$ (f-A) for condensation with the formyl group of compound (c) under formation of a carbon-carbon double bond, whereby the compound d-A-1) is synthesized. When $R^{4a}$ is $-COOR^9$, the compound (f-A) is a dialkyl malonate (e.g. dimethyl malonate, diethyl malonate, dipropyl malonate) and, when $R^{4a}$ is $-CN$, said compound is cyanoacetic acid or an alkyl ester thereof (e.g. methyl cyanoacetate, ethyl cyanoacetate, propyl cyanoacetate). The reaction can be carried out in a solvent, such as benzene, preferably in the presence of a base, such as pyridine, under refluxing conditions and will be complete in several to several tens of hours, preferably about 21 hours.

The compound (d-A-1) is then subjected to reduction reaction (catalytic hydrogenation) for reducing the double bond, whereby the compound (d-A-2) is synthesized. This reaction is carried out generally in an ether solvent, such as tetrahydrofuran, in the presence of a hydrogenation catalyst (e.g. palladium black, platinum black) at around room temperature, using hydrogen gas and will be complete in several hours, preferably about 4.5 hours.

Then, the compound (d-A-3) is synthesized by subjecting the compound (d-A-2) to saponification (hydrolysis) at its carboxylic acid ester moiety, followed by decarboxylation. The saponification can be effected using a conventional saponifying agent (e.g. potassium hydroxide, sodium hydroxide, sodium carbonate) under refluxing conditions and will be complete in several hours, preferably about 2.5 hours. The decarboxylation reaction is carried out in a solvent, such as benzene, following acidification of the reaction mixture with citric acid or the like, under refluxing conditions and will be complete in several tens of minutes to several hours, preferably about 1 hour.

Finally, the compound (d-A-3) is subjected to deprotection of the amino group to give the compound (a). The deprotection reaction can be carried out by a method conventionally used in eliminating amino-protecting groups. For example, the reaction can be conducted using acetic acid or the like under acidic conditions at a temperature in the vicinity of 80° C. for several tens of minutes to several hours, preferably about 30 minutes.

The objective compound obtained in each step can be purified in a conventional manner, for example by any of various chromatographic techniques and/or recrystallization, according to physical characteristics of said compound.

(Synthetic method B)

This synthetic method, which is described below in further detail, can be used in synthesizing those compounds (a) in which $R^4$ is $-(CH_2)_mCN$ or $-(CH_2)_mCOOH$. The method may be schematically illustrated by the following reaction scheme.

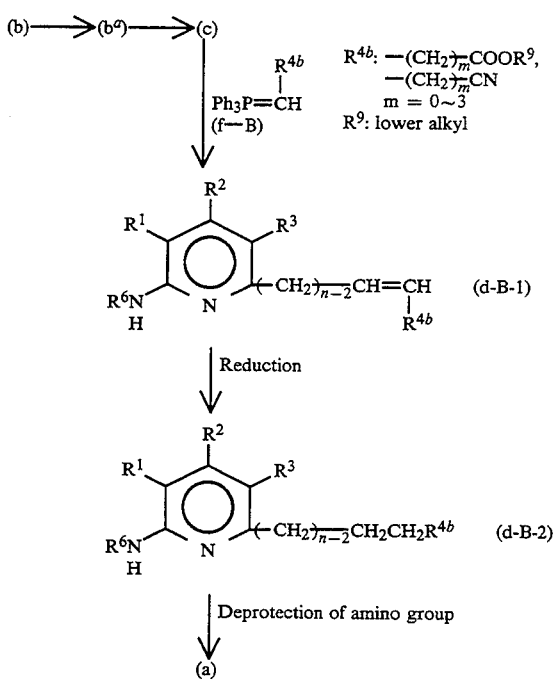

The compound (c) synthesized in the same manner as in synthetic method A is subjected to reaction (Wittig reaction) with a compound of the formula $Ph_3P=CHR^{4b}$ (f-B) (Wittig reagent) for condensation of the latter compound with the formyl group of compound (c) under formation of a carbon-carbon double bond, whereby the compound (d-B-1) is synthesized. The compound (f-B) to be used here includes, as specific examples thereof, $Ph_3P=CHCN$, $Ph_3P=CH(CH_2)_2CN$, $Ph_3P=CH(CH_2)_2COOCH_3$, $Ph_3P=CH(CH_2)_2COOC_2H_5$, $Ph_3P=CH(CH_2)_3COOCH_3$, and $Ph_3P=CH(CH_2)_3COOC_2H_5$. The reaction is carried out in a solvent, such as benzene, under refluxing conditions and will be complete in several hours to several tens of hours.

Then, the compound (d-B-2) is synthesized from the compound (d-B-1) in the same manner as the reduction for synthesizing the compound (d-A-2) from the compound (d-A-1) in synthetic method A. The reaction period preferably amounts to several tens of hours, preferably about 15 hours. When the compound (d-B-2) is a carboxylic acid ester, said ester can then be saponified in the same manner as in synthetic method A.

Finally, the compound (a) is synthesized from the compound (d-B-2) in the same manner as the deprotection of the amino group for synthesizing the compound (a) from the compound (d-A-3) in synthetic method A.

The objective compound obtained in each step can be purified in a conventional manner, for example by any of various chromatographic techniques and/or recrystallization, according to physical characteristics of said compound.

(Synthetic method C)

In case the compound (a) obtained by synthetic method A or B is a compound having a cyano group at position 6, said compound can be subjected to reduction reaction for converting $-CN$ to $-CH_2NH_2$. This reduction reaction can be carried out in the same manner as the reduction reaction for synthesizing the compound (d-A-2) from the compound (d-A-1) in synthetic method A.

[Synthesis of compounds (e)]

The compound (e) can be prepared by reacting the amino group at position 2 of the compound (a) with a reducing terminus of a carbohydrate including monosaccharide, oligosaccharide, polysaccharide, glycosaminoglycan or mixture thereof to give a Schiff base and reducing the Schiff base for the formation of a $-CH_2NH-$ bond. In the formula (e), the carbohydrate residue is represented by $R^8$.

[Organic compounds to be reacted with the functional groups]

The organic compounds to be reacted with the compounds (a) or (e) to form conjugates are not limited to any particular species as long as the conjugates are analyzable by fluorescence spectrometry. Preferred as said organic compounds are biological substances such as carbohydrates (polysaccharides, glycosaminoglycans, oligosaccharides, monosaccharides, etc.), proteins (physiologically active proteins, antibodies, enzymes, polypeptides, etc.), amino acids, lipids and nucleic acids.

[Reaction of the functional groups (synthesis of conjugates)]

The mode of reaction between the functional groups and the organic compounds is not limited to any particular one but includes, as preferred examples, the amide bond formation reaction, ester bond formation reaction, Schiff base formation reaction, amidine formation reaction, and disulfide bond formation reaction, among others.

The compounds of the invention and/or the organic compounds may be subjected to various reactions, for example condensation reaction, after introduction of an activating group into the functional group or groups thereof in a conventional manner. Thus, for instance, when the functional group to be involved in a condensation reaction is a carboxyl group, said carboxyl group can be activated by esterification with N-hydroxysuccinimide, p-nitrophenol or the like or by conversion to an azide group. In the condensation reaction, it is also possible to use a known condensing agent, for example a carbodiimide reagent such as dicyclohexylcarbodiimide (DCC), 1-ethyl-3-(3'-dimethylaminopropyl)carbodiimide (EDC) or 1-benzyl-3-dimethylaminopropylcarbodiimide tosylate.

For example, a carbohydrate-organic compound conjugates can be prepared by reacting the amino group at position 2 of a compound (a) with a reducing terminus of a carbohydrate to give a compound (e), separating and purifying the compound (e) as necessary by fractionation means such as high-performance liquid chromatography (HPLC), detecting the desired conjugate by means of its fluorescence spectrum and further reacting the functional group $R^4$ at position 6 of the compound (e) with an organic compound (e.g. carbohydrate, protein, oligopeptide, amino acid, nucleic acid, lipid, polymer resin) having a functional group capable of reacting with $R^4$.

Preferred as a carbohydrate to be bound to the compound (a) are carbohydrates derived from a biological substance such as glycoproteins, glycolipids, proteoglycans and the like or carbohydrate chains derived there from.

The above-mentioned Schiff base formation and the subsequent reduction each can be carried out by known methods [cf. JP-A-64-10177 and JP-A-1-141356; J. Biochem., 95, 197-203 (1984); Tanpakushitsu, Kakusan, Koso, 36(1), 63-68 (1991)]. Thus, Schiff bases can be formed by reacting a carbohydrate with about 20 to 100 equivalents, relative to the carbohydrate, of a compound (a) in an organic solvent, such as pyridine, in the presence of an inorganic acid, such as hydrochloric acid or hydrofluoric acid, or an organic acid, such as acetic acid or trifluoroacetic acid, at ordinary temperature to 100° C. for several minutes to several hours, preferably at about 90° C., and at pH 3 to 6.4, for about 1 to 3 hours. For reducing the Schiff bases, any of reducing agents commonly used in reducing Schiff bases may be used. Particularly preferred, however, are volatile borane complexes (e.g. borane-dimethylamine complex, borane-triethylamine complex, borane-pyridine complex, etc.), sodium borohydride, sodium cyanoborohydride ($NaBH_3CN$) and the like. The reduction reaction is carried out at ordinary temperature to 100° C. for 1 to 10 hours, preferably at about 80° to 90° C. for about 1 hour.

The compounds (a) of the present invention, when reacted and coupled, via the amino group at position 2 of the pyridine ring and the above-mentioned functional group at position 6, respectively with optionally selected organic compounds, in particular biological substances such as carbohydrates, proteins, amino acids, nucleic acids, lipids, etc., can crosslink the organic compounds with each other and thus can give-neoconjugates analogous to known conjugated compounds (e.g. conjugated carbohydrates, conjugated lipids, conjugated proteins) or model compounds therefor or can serve as marker compounds for fluorescence labeling of such organic compounds, hence are applicable to identification, assay, preparation and/or purification of various compounds, among others.

The organic compounds fluorescence-labeled with a compound (a) can be fractionated by known fractionation methods (e.g. chromatography, for example high-performance liquid chromatography, thin layer chromatography, gas chromatography; electrophoresis) and subjected to fluorescence spectrometry, whereby the desired organic compounds can be isolated, structurally analyzed and/or assayed.

The compound (a) is useful for analysis of carbohydrate Chains contained in a biological substance. Namely, the compound (a) is reacted with a carbohydrate mixture to give conjugates, i.e., compounds (e), fractionating the resulting conjugates mixture, measuring fluorescence spectrum of each fraction to determine each carbohydrate component.

The compounds (e) of the present invention as such are useful not only as starting materials for producing the above-mentioned neoconjugates, which can be regarded as neoglycoconjugates analogous to conjugated carbohydrates, but also as fluorescent labeling agents. Such neoglycoconjugates can be applied in studying the carbohydrates with regard to their antigenecity, preparing antibodies thereto, or analyzing the structure thereof.

For example, the compound (e), which is prepared by reacting the compound (a) with a carbohydrate chain derived from a biological substance, is reacted with an organic substance such as carbohydrate, protein, oligopeptide, amino acid, nucleic acid, lipid and polymer resin so as to bind the functional group $R^4$ of the compound (e) to the functional group of the organic substance and measuring fluorescence spectrum of the resulting conjugate. Then, the conjugate can be subjected to analysis of antigenecity and the like.

For use as fluorescent labeling agents, the compounds (a) and (e) of the invention may be in the form of salts (e.g. hydrochloride, acetate) or may be stored in a solid or liquid state. When stored in a liquid state, the compound of the invention is dissolved in a solvent such as ethers, alcohols, dimethylformamide, dimethylsulfoxide, pyridine, amines and the like. If desired, they may be used in admixture or combination with various stabilizers and other additives known in the art.

The compounds (a) can be used also as crosslinking agents in the same mode of application as in the above-mentioned case of fluorescent labeling agents.

The 2-aminopyridine derivatives of the invention, when reacted and coupled with carbohydrates, proteins, lipids and the like, can form neoconjugates analogous to conjugated carbohydrates, conjugated lipids, conjugated proteins, and such neoconjugates can be analyzed by various fluorescence spectrometric techniques in identifying, assaying, preparing and/or purifying, for instance, various such compounds, in particular biological macromolecules complicated in structure, for example antigens and antibodies, by various chromatographic techniques, gel electrophoresis, immunoelectrophoresis, immunoassay or the like. Therefore, the invention can provide powerful analytical means utilizable in a very wide range of study of complicated compounds, in particular biological macromolecules.

The following examples illustrate the invention in further detail but are by no means limitative of the scope of the invention.

EXAMPLE 1

Synthesis of 2-amino-6-(2-carboxyethyl)pyridine

The compound (b-1) (m.p. 72°-73° C.) shown below was synthesized by known techniques in the following manner.

2-Amino-6-methylpyridine was acetylated to protect the 2-amino group thereof and then the 6-methyl group thereof was oxidized. The oxidation product was deacetylated and the carboxyl group of the thus-obtained 2-amino-6-carboxy-pyridine was ethyl-esterified. The subsequent process is explained referring to the synthesis route shown below.

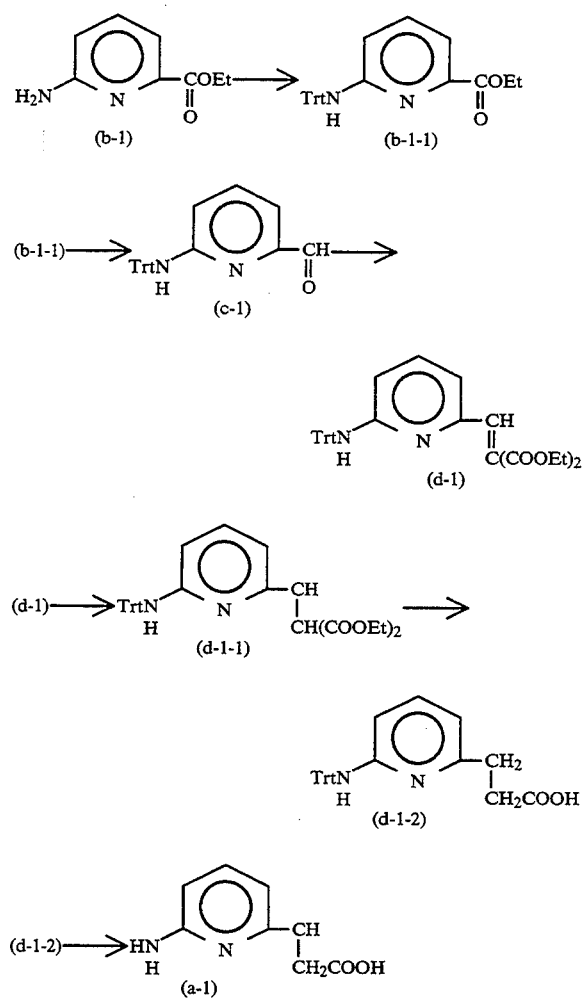

The compound (b-1) (0.10 g) was dissolved in 1.6 ml of a mixed solvent composed of chloroform and triethylamine (18:1 ), 0.17 g of trityl chloride was added thereto, and the mixture was stirred at room temperature for 4.5 hours for protecting the 2-amino group with a trityl (Trt) group, whereby the compound (b-1-1) (m.p. 53°–58° C.) was obtained in 88% yield. The compound (b-1-1) (4.0 g) prepared in this manner was dissolved in 120 g of toluene, and reduction of the COOEt group (Et being ethyl) to a formyl group was performed using DIBAL-H at −70° C. for 0.5 hours, whereby the compound (c-1), 2-tritylamino-6-formylpyridine (m.p. 208°–209° C. (dec.)), was obtained in 85% yield. The compound (c-1) (2.2 g) was dissolved in 53 g of benzene, 1.6 g of diethyl malonate [$CH_2(COOEt)_2$] and a few drops of piperidine were added, and the mixture was refluxed for 21 hours for causing condensation of diethyl malonate with said formyl group, whereby the compound (d-1) (m.p. 146°–150° C.) was obtained in 84% yield. This compound (d-1) (1.3 g) was dissolved in 30 g of tetrahydrofuran-methanol (7:1) and subjected to catalytic reduction by stirring in a hydrogen stream in the presence of palladium black for 4.5 hours to give the compound (d-1-1) (m.p. 72°–74° C.) in 99% yield. This compound (d-1-1) was dissolved in 10 N potassium hydroxide (KOH) solution and the solution was refluxed for 2.5 hours for saponification, followed by addition of citric acid. The compound thus produced was dissolved in benzene and heated under reflux for 1 hour for decarboxylation to give the compound (d-1-2) (m.p. 120° C.) in 100% yield. The compound (d-1-2) thus obtained was dissolved in 50% acetic acid and the trityl group was eliminated by reacting at 80° C. for 30 minutes to give the desired 2-amino-6-(2-carboxyethyl)-pyridine (a-1) (m.p. 166° C. (dec.)) in 97% yield. The excitation wavelength λex was 305 $n_m$, and the fluorescence wavelength λem was 367 nm. The overall yield from the starting compound (b-1) was about 55%.

The structure of each of the above-mentioned compounds (b-1) to (a-1) was confirmed by 1H NMR and MS (mass spectrometry) or further by elemental analysis. The results obtained are shown below.

Compound (b-1-1): Ethyl 2-tritylaminopicolinate $^1$H NMR (270 MHz, CDCl$_3$), δ=7.34–7.07 (17H, m, Ph-, H-3,4 ), 6.46 (1H, s, —NH—), 5.96 (1H, dd, $J_{3,5}$=8 Hz, $J_{3,5}$=1 Hz, H-5), 4.40 (2H, q, J=7 Hz, methylene of —CO$_2$CH$_2$CH$_3$), 1.38 (3H, t, J=7 Hz, methylene of —CH$_2$CH$_3$). positive EI-MS m/z 408 (M+). Elemental analysis Found: C, 79.55; H, 6.02; N, 6.57 Calcd. for C$_{27}$H$_{24}$O$_2$N$_2$: C, 79.39; H, 5.92; N, 6.86.

Compound (c-1 ): 2-Tritylamino-6-formylpyridine $^1$H NMR (270 MHz, CDCl$_3$), δ=9.80 (1H, s, —CHO), 7.35–7.14 (17H, m, Ph-, H-3,4), 6.35 (1H, s, —NH—), 6.06 (1H, dd, $J_{4,5}$=8 Hz, $J_{3,5}$=1 Hz, H-5). positive EI-MS m/z 364 (M+). Elemental analysis Found: C, 82.47; H, 5.58; N, 7.58; Calcd. for C$_{25}$H$_{20}$ON$_2$: C, 82.39; H, 5.53; N, 7.69.

Compound (d-1): Ethyl 2-ethoxycarbonyl-3-(6-tritylamino-2-pyridyl)acrylate $^1$H NMR (270 MHz, CDCl$_3$), δ=7.45 (1H, s, —CH=C), 7.31–7.22 (15H, m, Ph-), 7.04 (1H, dd, J=8 Hz, 7 Hz, H-4), 6.64 (1H, d, J=7 Hz, H-3 or 5), 5.99 (1H, s, —NH—), 5.78 (1H, d, J=8 Hz, H-5 or 3), 4.29 (4H, q, J=7 Hz, methylene of —CO$_2$CH$_2$CH$_3$), 1.34–1.25 (6H, m, J=7 Hz, methylene of —CH$_2$CH$_3$ ). positive EI-MS m/z 506 (M+). Elemental analysis Found: C, 76.03; H, 5.97; N, 5.52; Calcd. for C$_{32}$H$_{30}$O$_4$N$_2$: C, 75.87; H, 5.97; N, 5.53.

Compound (d-1-1): Diethyl (6-tritylamino-2-pyridyl)-methylmalonate $^1$H NMR (270 MHz, CDCl$_3$), δ=7.35–7.18 (15H, m, Ph-), 6.94 (1H, dd, J=8 Hz, 7 Hz, H-4), 6.37 (1H, d, J=7 Hz, H-3 or 5), 5.94 (1H, s, —NH—), 5.66 (1H, d, J=8 Hz, H-5 or 3), 4.15 (4H, q, J=7 Hz, methylene of —CO$_2$CH$_2$CH$_3$), 3.95 (1H, t, J=7 Hz, methine of —CH$_2$CH—), 3.14 (2H, d, J=7 Hz, methylene of —CH$_2$CH—), 1.20 (6H, m, J=7 Hz, methyl of —CH$_2$CH$_3$ ). positive EI-MS m/z 508 (M+). Elemental analysis Found: C, 75.76; H, 6.34; N, 5.45; Calcd. for C$_{32}$H$_{32}$O$_4$N$_2$: C, 75.57; H, 6.34; N, 5.51.

Compound (d-1-2): 2-Tritylamino-6-(2-carboxyethyl)-pyridine $^1$H NMR (270 MHz, CDCl$_3$), δ=7.35–7.21 (15H, m, Ph-, —NH—), 7.13 (1H, dd, J=8 Hz, 7 Hz, H-4), 6.46 (1H, d, J=7Hz, H-3 or 5), 5.88 (1H, d, J=8 Hz, H-5 or 3), 3.01 (2H, t, J=6 Hz, α or βH of —CH$_2$CH$_2$—), 2.82 (2H, t, J=6 Hz, α or βH of —CH$_2$CH$_2$—). positive FAB-MS m/z 409 (M+H)+. Elemental analysis Found: C, 77.78; H, 5.92; N, 6.65; Calcd. for C$_{27}$H$_{24}$O$_2$N$_2$·0.5H$_2$O: C, 77.67; H, 6.04; N, 6.71.

Compound (a-1): 2-Amino-6-(2-carboxyethyl)pyridine $^1$H NMR (270 MHz, D$_2$O, DSS), δ=7.79 (1H, dd, J=9 Hz, 7Hz, H-4), 6.81 (1H, d, J=9 Hz, H-3 or 5), 6.73 (1H, d, J=7Hz, H-5 or 3), 2.96 (2H, t, J=7 Hz, α or βH of —CH$_2$CH$_2$—), 2.58 (2H, t, J=6 Hz, α or βH of —CH$_2$CH$_2$—). positive FAB-MS m/z 167 (M+H)$^+$.

EXAMPLE 2

Synthesis of 2-amino-6-(2-cyanoethyl)pyridine

The above compound was synthesized from the compound (c-1) obtained in Example 1, via the route shown below.

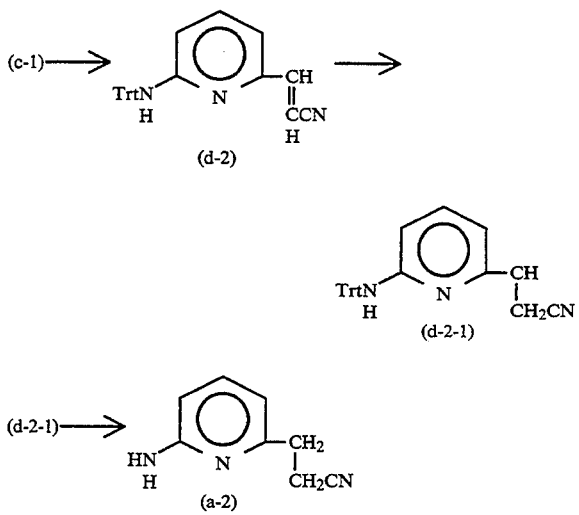

Thus, 2.5 g of the compound (c-1) was dissolved in 17 g of benzene, 10.1 g of Ph$_3$P=CHCN was added thereto and the Wittig reaction was conducted to give the compound (d-2) (identified by $^1$H NMR and MS; yield 96%). The compound (d-2) (1.4 g) was dissolved in 45 g of tetrahydrofuran-methanol (7:1) and subjected to catalytic reduction by stirring the solution in the presence of palladium black in a hydrogen stream at 3 atmospheres for 15 hours, whereby the compound (d-2-1) was obtained in 100% yield. The thus-obtained compound (d-2-1) was dissolved in 50% acetic acid and the trityl group was eliminated by treating at 80° C. for 30 minutes to give the desired compound 2-amino-6-(2-cyanoethyl)pyridine (a-2) in 100% yield (m.p. 66°–68° C.). The excitation wavelength λex was 295 nm and the fluorescence wavelength λem was 364 nm.

The structure of each of the compounds mentioned above was confirmed by $^1$H NMR and MS or further by elemental analysis. The results obtained are shown below.

Compound (d-2): 3-(6-Tritylamino-2-pyridyl)-propenenitrile $^1$H NMR (270 MHz, CDCl$_3$), δ=7.35–7.19 (15H, m, Ph-), 7.12 (1H, dd, J=8 Hz, 7 Hz, H-4), 7.12 (1H, d, J=16 Hz, βH of—CH=CHCN), 6.50 (1H, d, J=7 Hz, H-3 or 5), 6.17 (1H, d, J=16 Hz, αH of —CH=CHCN), 6.05 (1H, s, —NH—), 6.03 (1H, d, J=8 Hz, H-5 or 3). positive FAB-MS m/z 388 (M+H)$^+$. Elemental analysis Found: C, 82.90; H, 5.41; N, 10.47; Calculated for C$_{27}$H$_{21}$N$_3$.2H$_2$O: C, 82.92; H, 5.52; N, 10.7.

Compound (d-2-1): 2-Tritylamino-6-(2-cyanoethyl)-pyridine $^1$H NMR (270 MHz, CDCl$_3$), δ=7.35–7.19 (15H, m, Ph-), 7.04 (1H, dd, J=8 Hz, 7 Hz, H-4), 6.38 (1H, d, J=7 Hz, H-3 or 5), 5.93 (1H, s, —NH—), 5.84 (1H, d, J=8 Hz, H-5 or 3), 2.80 (2H, t, J=7 Hz, β or αH of —CH$_2$CH$_2$CN), 2.57 (2H, t, J=7Hz, α or βH of —CH$_2$CH$_2$CN). positive FAB-MS m/z 390 (M+H)$^+$.

Compound (a-2): 2-Amino-6-(2-cyanoethyl)pyridine $^1$H NMR (270 MHz, CDCl$_3$), δ=7.45 (1H, dd, J=8 Hz, 7 Hz, H-4), 6.59 (1H, d, J=7 Hz, H-3 or 5), 6.46 (1H, d, J=8 Hz, H-5 or 3), 4.89 (2H, bs, —NH$_2$), 2.97 (2H, t, J=7 Hz, β or αH of —CH$_2$CH$_2$CN ), 2.82 (2H, t, J=7 Hz, α or βH of —CH$_2$CH$_2$CN ). positive EI-MS m/z 147 (M+).

EXAMPLE 3

A conjugate of 2-amino-6-(2-carboxyethyl)pyridine (a-1) with D-glucose (D-Glc) or D-mannose (D-Man) was synthesized by the route shown below.

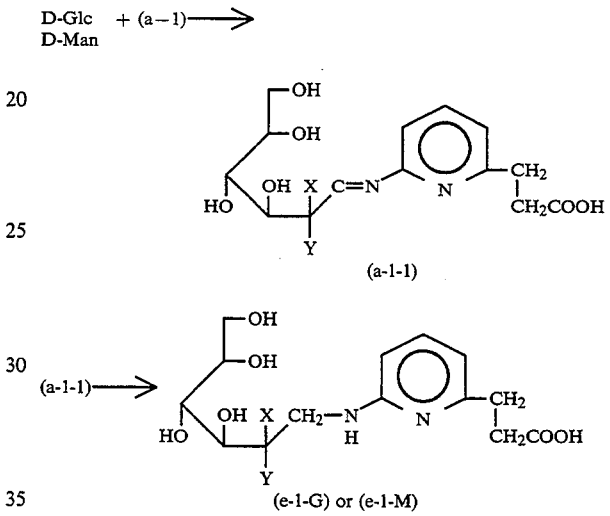

Thus, D-Glc or D-Man and 20 equivalents, relative to D-Glc or D-Man, of the compound (a-1) were dissolved in a mixed solvent composed of acetic acid and pyridine (1:40) to a concentration of the compound (a-1) of 0.4 μmol/ml, and the solution was treated at 90° C. and at pH 6.4 for 1 hour to Synthesize the Schiff base compound (a-1-1) (D-Glc type: X=H, Y=OH; D-Man type: X=OH, Y=H). The compound (a-1-1) obtained was dissolved in acetic acid-pyridine (1:40) and reduced with borane-dimethylamine complex (BH$_3$.Me$_2$NH) at 80° C. for 1 hour, to give the compound, namely (e-1-G) (X=H, Y=OH) or (e-1-M) (X=OH, Y=H), in 50–70% yield.

When D-Glc was used as the starting material, the compound (e-1-G) and its 2-epimer [compound (e-1-M)] were found in a ratio of about 95:5.

When D-Man was used as the starting material, the compound (e-1-M) and its 2-epimer [compound (e-1-G)] were formed in a ratio of about 95:5. The compounds (e-1-G) and (e-1-M) obtained were identified by $^1$H NMR and MS.

Variation in the amount of compound (a-1) in the Schiff base formation reaction within the range of 20 to 100 equivalents or variation in the time of heating within the range of 1 to 3 hours did not affect the yield or the epimerization.

The compounds (e-1-G) and (e-1-M) could be separated by HPLC under the following conditions:

Column: Cosmosil 5C18AR [20 mm (ID)×250 mm (L)] (Nacalai Tesque);
Eluent system: Acetonitrile-0.1M aqueous ammonium acetate solution (pH 6.85);

Concentration gradient: 0 to 10% (0.5%/minute) to 50% (2%/minute);
Flow rate: 8 ml/minute;
Detection: UV 300 nm.

EXAMPLE 4

A conjugate of the compound (e-1-G) as synthesized in Example 3 with an amino acid derivative [$O^1$-methyl-$N^2$-acetyllysine hydrochloride ($N^2$-Ac-Lys-OMe)] was prepared as a fluorescence-labeled carbohydrate-protein neoconjugate model in the following manner.

The compound (e-1-G) was dissolved in water to a concentration of 20% by weight, together with 0.5 equivalent, relative to the compound (e-1-G), of the condensing agent EDC and 2.5 equivalents, on the same basis, of EDC.HCl, followed by addition of 10% by weight, relative to water, of 1-hydroxybenzotriazole. The mixture was stirred at pH 5 to 6 for about 20 hours to give the fluorescence-labeled neoconjugate (f) of the formula

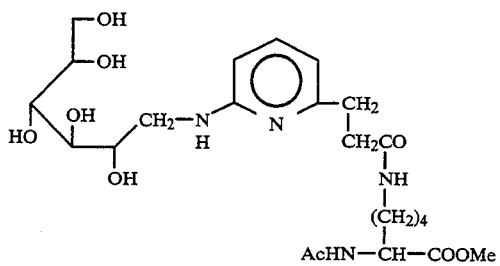

(f)

in 42% yield.

The compound (f) obtained was identified by 1H NMR and MS (FAB) and it was confirmed that the compound contained an amide bond derived from the ε-amino group of lysine and the carboxyl group of the compound (e-1-G).

EXAMPLE 5

2-Acetylamino-6-(3-acetylaminopropyl)pyridine was synthesized in the following manner.

2-Acetylamino-6-(2-cyanoethyl)pyridine (11.5 mg, 78 μmol) was dissolved in 25% ammonia water (3.0 ml) and, after purging with nitrogen, palladium black (30 mg) was added thereto. After repurging with nitrogen, the mixture was stirred at room temperature under a hydrogen stream at 9 atmospheres for 28 hours. After nitrogen purging, the palladium black was filtered off and the filtrate was concentrated under reduced pressure. Chloroform (500 μl) was added to the residue and, the mixture was cooled with ice and, after addition of acetic anhydride (100 μl, 1.1 mmol), stirred for 10 minutes. After allowing the temperature to rise to room temperature, stirring was continued for 5 hours. After cooling with ice, methanol (1.0 ml) was added and the mixture was stirred for 1 hour and then concentrated under reduced pressure. The residue was purified by silica gel column chromatography [silica gel 10 g, chloroform-methanol (19:1)→(15:1)] to give 2-acetylamino-6-(3-acetylaminopropyl)pyridine as a colorless solid (Yield 6 mg (51%)).

$^1$H NMR (270 MHz, CDCl$_3$), δ=9.25 (1H, bs, —CH$_2$NHAc), 8.10 (1H, d, J=8 Hz, H-3 or 5), 7.66 (1H, dd, J=8 Hz, 7 Hz, H-4), 6.91 (1H, d, J=7Hz, H-3 or 5), 5.74 (1H, bs, 2—NH—Ac), 3.29 (2H, m, —CH$_2$NHAc), 2.71 (2H, t, J=7 Hz, αH of 6-CH$_2$CH$_2$CH$_2$NHAc), 2.21 (3H, s, 2-NHCOCH$_3$ ), 1.97 (3H, s, —CH$_2$NHCOCH$_3$), 1.89 (2H, m, βH of —CH$_2$CH$_2$CH$_2$—). positive EI-MS m/z 235 (M+).

While the invention has been described in detail and with reference to specific examples thereof, it will be apparent to one skilled in the art that various changes and modifications can be made therein without departing from the spirit and scope thereof.

What is claimed is:

1. A 2-aminopyridine of the formula (a)

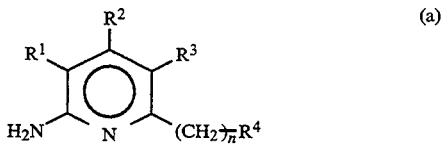

(a)

wherein $R^1$, $R^2$ and $R^3$ are the same or different and each represents a hydrogen atom or a lower alkyl group containing 1 to 4 carbon atoms, $R^4$ represents a cyanoalkyl group of the formula —(CH$_2$)$_m$CN, an aminoalkyl group, an alkyloxycarbonylamino group, a maleimido group, or a halogen atom, n is an integer of 2 to 20 and m is 0 or an integer of 1 to 3.

* * * * *